United States Patent [19]

Reynolds

[11] Patent Number: 4,880,973

[45] Date of Patent: Nov. 14, 1989

[54] GROUND RADON FLUX SAMPLING DEVICE

[76] Inventor: John D. Reynolds, Star Route, Box 124, Topping, Va. 23169

[21] Appl. No.: 219,632

[22] Filed: Jul. 15, 1988

[51] Int. Cl.$^4$ ............................................. G01V 5/00
[52] U.S. Cl. .................................... 250/253; 250/255
[58] Field of Search ............. 250/253, 255, 364, 472.1

[56] References Cited

U.S. PATENT DOCUMENTS

| | | | |
|---|---|---|---|
| 3,968,371 | 7/1976 | Greendale | 250/380 |
| 4,017,731 | 4/1977 | Howell et al. | 250/253 |
| 4,352,014 | 9/1982 | Powell | 250/253 |
| 4,385,236 | 5/1983 | Hassib et al. | 250/472.1 |
| 4,518,860 | 5/1985 | Alter et al. | 250/253 |
| 4,700,067 | 10/1987 | Carossi et al. | 250/380 |
| 4,700,070 | 10/1987 | Kovac | 250/304 |

OTHER PUBLICATIONS

"Radon Flux Measurement Technology," Freeman and Hartley, *Indoor Radon*, Feb. 1986.

Primary Examiner—Janice A. Howell
Assistant Examiner—T. Nguyen

[57] ABSTRACT

An in-situ radon flux sampling device for accommodating a canister (22) of radon adsorption material for measurement of radon gas emanating from the ground. The device includes a holder body (10) for the removable cannister (22). The body (10) is inserted into the ground, thusly providing for sealing with and steady support in the ground. The holder body (10) is equipped with a plurality of vent holes (29) to keep radon gas flow and concentration sampling conditions substantially the same as would be encountered above the soil in absence of the sampling device. The holder body (10) for further accomodates a removable barrier filter (26) for substantial avoidance of contamination of the adsorption material by particulate matter and moisture from the soil, as well as by moisture from the atmosphere. The holder body (10) includes a removable cap (12) having one or more vent holes (14) therein. The holder body (10) and its cap (12) are easily cleanable and reusable.

12 Claims, 2 Drawing Sheets

GROUND RADON FLUX SAMPLING DEVICE

BACKGROUND OF THE INVENTION

FIELD OF THE INVENTION

This invention relates to sampling measurement devices for radon gas emanating from the ground, and particularly to such devices that are placed on top of the soil and that are comprised of activated charcoal or other material which is evaluated subsequently to the in-situ sampling procedure at a remote laboratory facility.

II. PRIOR ART AND OTHER CONSIDERATIONS

Various devices for sampling and measurement of ground radon emission has found increasingly widespread application in recent years. Accurate radon emission measurement directly on site is relatively complex and costly, largely due to the in-situ need for sophisticated instrumentation and personnel with specialized training. Accordingly, sampling procedures have been developed that rely, for instance, on adsorption of radon gas released from the ground at a test site on an appropriate medium. The medium is subsequently analyzed in a laboratory to provide a measure of the radon emission sampled.

For example, prior art radon sampling procedures and devices are described by Freeman and Hartley, "Radon Flux Measurement Technology," *Indoor Radon*, February, 1986. Among other devices and procedures, Freeman and Hartley describe the use of activated charcoal canisters, whereby such a canister is placed in close contact with the soil for a certain time exposure; the canister is thereafter removed and sealed; and, the amount of radon activity on the activated charcoal is subsequently determined from gamma spectroscopy. A used activated charcoal canister is shown in FIG. 3 of the paper in form of a short disk-shaped container that is open in the bottom and, with exception of a small vent hole, closed at the top. The container holds a layer of activated charcoal between retaining and supporting components.

Other prior art sampling and measuring devices are known. For instance, U.S. Pat. No. 4,518,860 to Alter et al. describes a compact radon detector in a housing of tubular structure. U.S. Pat. No. 4,700,070 to Kovac discloses a radon detection apparatus and method using a measured amount of charcoal for collecting radon within a cylindrical housing. U.S. Pat. No. 4,700,067 to Carossi et al. discloses an apparatus for checking atmospheric pollution.

Field use of prior art activated charcoal canisters, particularly when conducted by persons not knowledgeable in the intricacies of the involved sampling and measurement mechanisms, results in inaccurate and unreliable measurements. Such inaccuracies are often attributable to faulty sealing of the canister to the ground surface and to contamination of the charcoal by soil particles, dust, and soil and atmospheric moisture.

Additionally, prior art charcoal canisters do not necessarily sample radon gas emanating from the soil at the same concentration and at the same rate of flow as that normally released to ambient in absence of a sampling device. Radon concentration tends to increase with time in prior art sampling devices, as radon tends to diffuse back into the soil and thusly affects the measurements unpredictably.

It is therefore an object of the invention to provide a ground radon flux sampling device that provides accurate and reliable measurements of radon gas emission.

An advantage of the present invention is the provision of a ground radon flux sampling device that is at least partially reusable.

SUMMARY OF THE INVENTION

A ground radon flux sampling device comprises a holder body for a charcoal canister. The holder body is insertable into the ground, resulting in reliable sealing of the device to and steady support in the soil. The holder is provided with a plurality of vent holes in locations just below the canister support level (above the soil level when installed). The vent holes effect radon gas flow conditions, and thus also radon concentrations, within the device, so that such conditions are substantially the same as would be normally encountered above the soil in absence of a sampling device. In addition, a barrier filter that does not absorb water and that allows free passage of radon gas is provided in the holder in a location slightly above ground level when the device is installed in the soil. The barrier filter substantially minimizes or avoids contamination of the charcoal by moisture and soil particles or dust.

The holder for the charcoal canister further comprises an easily removable cap that closes the upper holder opening. The cap is provided with one or more vent holes.

The holder is equipped internally with supports and retainers for the easily insertable and removable barrier filter and for the easily replaceable charcoal canister, whereby different size canisters are accommodatable. Holder and cap are easily cleanable and reusable thereafter.

Canisters for radon adsorption measurement purposes other than those containing activated charcoal can be utilized within the holder device of the invention equally well. In some may situations, the holder device may be used with the barrier filter removed provided that the canister itself comprises an appropriate barrier filter.

The present invention of a ground radon flux sampling device avoids the described disadvantages in prior art radon testing by provision of a special holder device for activated charcoal canister to promote reliable sealing of the device to the soil surface in installation, to avoid contamination of the activated charcoal by soil particles and by moisture from soil and atmosphere, and to keep the flow of radon gas (emanating from the soil and being adsorbed on the charcoal in the canister) substantially at the same rate of flow a that normally moving from the soil into the atmosphere in absence of the sampling device; thusly avoiding undesirable increases of radon concentration in the volume between soil level and the charcoal.

BRIEF DESCRIPTION OF THE DRAWINGS

The foregoing and other objects, features and advantages of the invention will be apparent from the following more particular description of referred embodiments of the invention, as illustrated in the accompanying drawings. The drawings are schematic and not necessarily to scale, emphasis instead being placed upon illustrating principles of the invention.

DETAILED DESCRIPTION OF THE DRAWINGS

Figure 1:
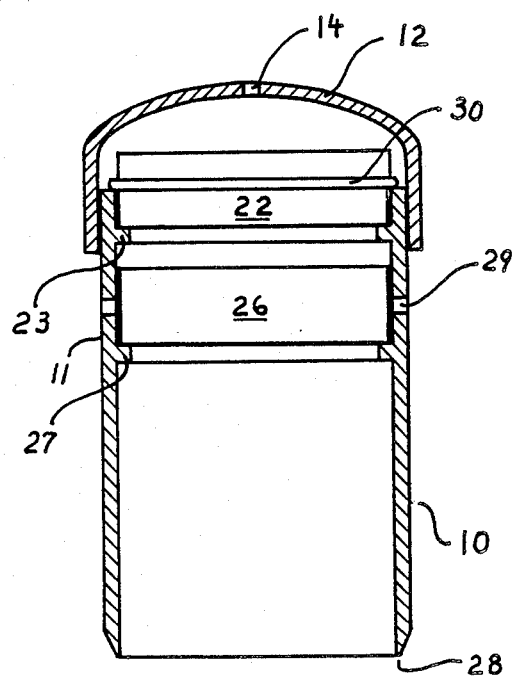
FIG. 1 is a sectioned side view of a ground radon flux sampling device according to an embodiment of the present invention.

Referring to the drawing in FIG. 1, numeral 10 designates a holder body of a ground radon flux sampling device of the present invention. The holder body 10 is a hollow cylinder with two open ends. The cylindrical member 10 serves as a sidewall 11. A removable cap 12 covers its top end. Removable cap 12, that fits over the top opening of holder body 10, is provided with one or more vent holes, represented here by cap vent hole 14 in the cap's uppermost region. Along its lowermost edge 15 holder body 10 is provided with a sharp bottom edge 16 to facilitate insertion into the ground.

Holder body 10 retains therein a canister 22. Canister 22 includes a radon-adsorbing medium which may be activated charcoal or another suitable material. Canister 22 is substantially in the shape of a short cylinder and is supported on canister retainer stop 23. A barrier filter 26, also substantially in shape of a short cylinder, is supported on filter retainer stop 27. Retainer stops 23 and 27 are essentially ring shaped projections formed on the interior surface of holder body 10. In alternate embodiments, the stops 23 and 27 are a plurality of spider legs, or any other conventional structure serving the same purpose, whereby the structure of the stops protrudes inwardly from the inside periphery of holder body 10 in order to keep the canister 22 and the barrier filter 26 in their respective positions within the holder body 10. Stops 23 and 27 may be integral with the holder body 10 or they may be attached parts. Stop 23 is preferably sized and adapted to accommodate different size canisters.

A plurality of radial vent holes 29 perforates holder body 10 approximately at the mid-level of the location of barrier filter 26. Barrier filter 26 is comprised of a gas permeable fibrous filter material that permits free passage of radon gas. The filter material does not substantially absorb or adsorb moisture. Yet the filter material reduces access of moisture, and substantially blocks entry of dirt particles and dust that might otherwise enter the canister through the vent holes 16 or from the bottom opening of holder body 10, particularly during handling and operation of the device. In one embodiment, conventional scrubber pads are used for the barrier filter material, although any other equally suitable filter material may be used. Vent holes 29 provide filtered communication between the regions above and below barrier filter 26 and ambient atmosphere through the barrier filter.

Canister 22 is a conventional container holding a radon adsorbent medium, for example activated charcoal, and may be of the kind used in military gas masks. The housing of canister 22 may be of plastic, such as PVC (polyvinyl chloride), or metal, and commonly comprises appropriate support and retention means for the adsorption medium. The canister may be also of the non-charcoal-containing type, such as the commercially available so-called E-Perm detector. Canister ridge 30 is a peripheral ridge surrounding the periphery of some standard canisters that may be utilized, in addition to canister retainer stop 23, for retention and as insertion stop of canister 22 in holder body 10.

By way of example, the following approximate measurements and other details refer to a preferred embodiment of the holder device of the invention. Holder body 10 is made from a standard 4 inch diameter PVC pipe with a length of 6 inches. Similarly, cap 12 is a standard 4 inch PVC pipe cap (conventionally used for capping of 4 inch pipe) that is provided with a 3/16 inch diameter vent hole 14. Such standard pipe caps are commercially available in flat-topped and rounded-top versions, and either type can be used. Stops 23 and 27 are preferably thin annular PVC sections that are adhesively fastened within holes body 10. However, three equally spaced individual blocks adhesively bonded and/or screw-attached to the inner periphery of holder body 10 are used as an alternate. Holder body 10 is further provided with six equally spaced radial vent holes 16 of 3/16 inch diameter each.

Figure 2:
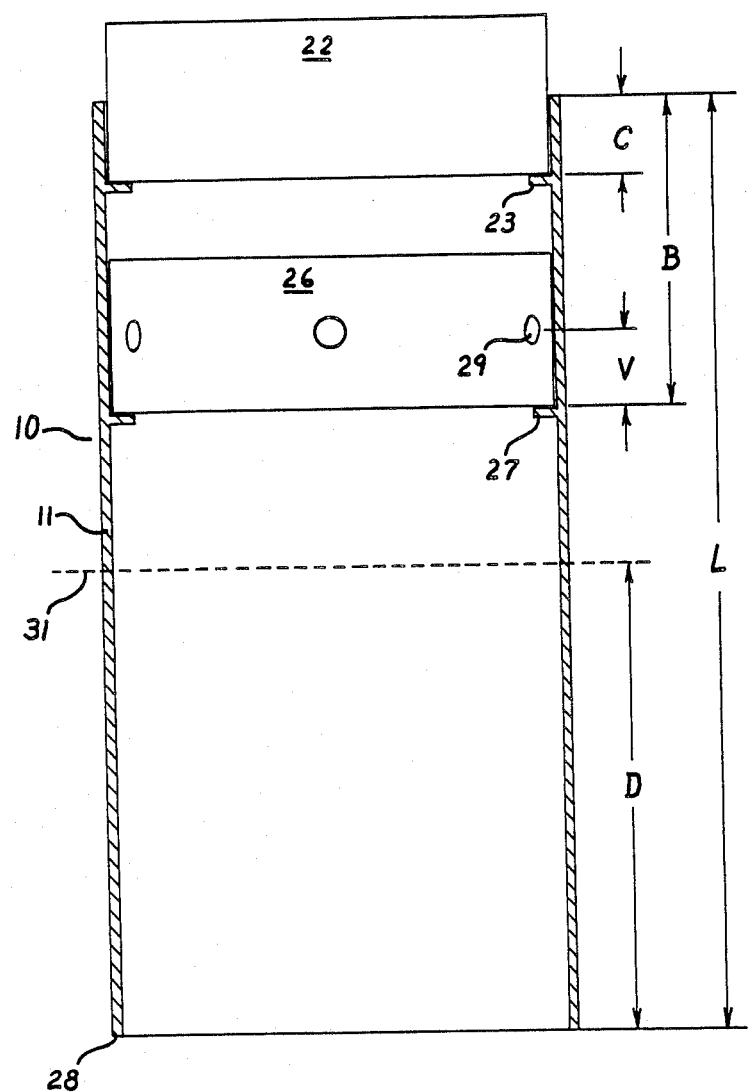
FIG. 2 is a diagrammatic representation of a side elevation of the sampling device of the embodiment of FIG. 1 showing preferred dimensions.

Further dimensional relationships of the preferred embodiment of the invention is provided by the schematic in FIG. 2, which diagrammatically represents holder body 10 including canister 22 and filter 26 in correctly inserted positions. Dimensions C and B represent distances from top of body 10 to the upper face (or support level) of stop 23 and stop 27 respectively, thusly also representing the distances to the lower edge or face of barrier filter 26 and canister 22, respectively. Length or height L of holder body 10 is 6 inches. Dimension B is 2 inches. Dimension C is ½ inch. Dimension D (from bottom of holder body 10 to dashed line 31 that represents ground surface level and therewith insertion depth) is a maximum of 3 inches. Dimension V, being ½ inch, indicates the location of vent holes 16 with respect to the position of barrier filter 26. Holes 16 are at the approximate mid-level of filter 26 whose thickness is approximately 1 inch. As indicated, an empty region extends for approximately 1 inch between ground surface level 31 and barrier filter 26, and another empty region extends for approximately ½ inch between the top of barrier filter 26 and the bottom of canister 22.

It will be appreciated that different materials, such as metal or other plastics, may be utilized for holder body 10 (including stops 23 and 27) and cap 12, and that these components may be manufactured by various conventional methods including, for instance, plastic molding.

In use, the sampling device, comprising holder body 10 capped with cap 12 and having a standard canister 22 and barrier filter 26 inserted therein, is inserted into the soil to a suitable depth (3 inches maximum for the described preferred embodiment). Radon gas released from the ground within the internal confines of holder body 10 permeates upwardly through barrier filter 26 and into canister 22, wherein it is substantially adsorbed by the adsorption medium contained therein. Cap vent hole 14 and holder vent holes 29 are so sized, and the number of holes 29 so chosen, to prevent build-up of radon gas concentration within the device and provide for substantially the same radon concentration conditions as if the radon gas were escaping from the open surface of the soil.

Barrier filter 26 reduces or substantially avoids entry of moisture, particles, and dust from the ground within the base of holder body 10 as well as from the ambient atmosphere through vent holes 29 into the adsorption medium within canister 22. Thusly erroneous radon measurement results due to absorption of radon by increased moisture is substantially avoided. Furthermore, contamination of the adsorption medium by dust and particles that can lead to inaccurate measurement results is also substantially avoided.

Before insertion into the soil, an originally sealed unused canister is unsealed and inserted into holder body 10 (that is equipped with a clean barrier filter 26) and holder body 10 is capped with cap 12. Exposure time depends on season and average temperature and is varied accordingly between approximately 24 hours and four days. Thereafter, canister 22 is removed, resealed, and provided to an appropriate laboratory facility for measurement and evaluation of the adsorbed radon. For example four inch charcoal canisters suited to the ground radon flux sampling device of the invention are commercially available from the DMA Analysis Group, Inc., Emmaus, Pa., who also provides the measurement and evaluation service subsequent to the described sampling procedure.

Holder body 10 and cap 12 may be reused repeatedly after cleaning. Barrier filter 26 is discarded and replaced by an unused one before any reuse of the device.

The ground radon flux sampling device of the present invention uses standard commercially available canisters containing radon adsorption media that have been used in prior art in various ways, particularly also by direct placement on the ground. As herein described, the sampling device of the present invention substantially reduces or avoids the described sources of inaccuracies and erroneous measurements by providing for adequate reliable contact seal to and support in the soil. Contamination of the adsorption medium is substantially avoided. The sampling device is vented to keep radon concentration within the device substantially the same as in the ambient atmosphere above the soil.

While the invention has been particularly shown and described with reference to preferred embodiments thereof, it will be understood by those skilled in the art that various changes and modifications in form and details may be made therein without departing from the spirit and scope of the invention.

The embodiments of the invention in which an exclusive property or privilege is claimed are defined as follows:

1. A radon sampling apparatus for measurement of radon gas emanating from the ground by adsorption of said radon gas on an adsorption medium within a canister, said apparatus comprising:

holder means having a sidewall for defining an internal region, said holder means having a first opening disposed in its top end and a second opening disposed in its bottom end for admission of said radon gas into said internal region, said canister being at least partially insertable into said holder means proximate said top end of said holder means;

a cap for capping said first opening, said cap having a vent opening therein;

first retainer means formed on said sidewall of said holder means for retaining said canister therein;

second retainer means formed on said sidewall of said holder means for retaining a replaceable filter means and in said internal region below said canister; and, venting means formed in said sidewall of said holder means to provide communication between said internal region and ambient atmosphere through said filter means.

2. A ground radon sampling apparatus according to claim 1, where in said holder means is substantially in the shape of cylindrical tube.

3. A ground radon sampling apparatus according to claim 2, wherein the material of said holder means and said cap is a PVC plastic.

4. A ground radon sampling apparatus according to claim 1, wherein said holder means and said cap are reusable.

5. A ground radon sampling apparatus according to claim 1, wherein said adsorption medium is activated charcoal.

6. A ground radon sampling apparatus according to claim 1, wherein said filter means comprises a scrubber pad.

7. A ground radon sampling apparatus according to claim 1, wherein said venting means comprises a plurality of holes disposed substantially in a mid plane of said replaceable filter means, said holes being approximately equally spaced about the periphery of said holder means.

8. A ground radon sampling apparatus according to claim 1, wherein a bottom end edge of said holder means defining said second opening is a substantially sharp edge.

9. A ground radon sampling apparatus according to claim 1, wherein one of said retainer means protrudes inwardly from the inside periphery of said sidewall of said holder means.

10. A ground radon sampling apparatus according to claim 1, wherein said first retainer means is adapted for retaining different sizes of said canister.

11. The ground radon sampling apparatus of claim 1, wherein a bottom end of said holder means is insertable into the ground to a ground insertion depth that is less than a distance from the said bottom end of said holder means to a lower face of the said replaceable filter means 12. A ground radon sampling apparatus according to claim 11, wherein said ground insertion depth is a maximum of about three inches.

* * * * *